United States Patent
Yoo

(10) Patent No.: US 9,945,314 B2
(45) Date of Patent: Apr. 17, 2018

(54) APPARATUS AND METHOD FOR CONTROLLING OXYGEN SENSOR

(71) Applicant: Hyundai Motor Company, Seoul (KR)

(72) Inventor: Jae-Woong Yoo, Whasung-Si (KR)

(73) Assignee: Hyundai Motor Company, Seoul (KR)

( * ) Notice: Subject to any disclaimer, the term of this patent is extended or adjusted under 35 U.S.C. 154(b) by 60 days.

(21) Appl. No.: 14/709,007

(22) Filed: May 11, 2015

(65) Prior Publication Data
US 2016/0123842 A1    May 5, 2016

(30) Foreign Application Priority Data
Oct. 29, 2014    (KR) .......................... 10-2014-0148131

(51) Int. Cl.
| | | |
|---|---|---|
| G01M 15/10 | (2006.01) | |
| F02D 41/22 | (2006.01) | |
| F02D 41/14 | (2006.01) | |
| G01N 27/407 | (2006.01) | |

(52) U.S. Cl.
CPC ....... F02D 41/222 (2013.01); F02D 41/1494 (2013.01); *F01N 2560/025* (2013.01); *F01N 2560/20* (2013.01); *F02D 41/1454* (2013.01); *G01N 27/407* (2013.01); *Y02T 10/40* (2013.01)

(58) Field of Classification Search
CPC .............. G01M 15/04; F01N 2560/025; F01N 2650/20; F01N 2900/0416; F02D 41/1454; G01N 27/407
USPC ........................................................ 73/1.06
See application file for complete search history.

(56) References Cited

U.S. PATENT DOCUMENTS

| | | | | |
|---|---|---|---|---|
| 5,454,259 A * | 10/1995 | Ishii | .................... | F02D 41/1495 73/114.72 |
| 5,928,303 A * | 7/1999 | Sakai | .................. | F02D 41/1474 701/109 |
| 6,850,870 B2 * | 2/2005 | Saga | .................... | F02D 41/1494 123/685 |
| 2003/0154053 A1 * | 8/2003 | Saga | .................... | F02D 41/1494 702/185 |
| 2004/0000493 A1 * | 1/2004 | Yasui | .................... | F02D 41/222 205/775 |

(Continued)

FOREIGN PATENT DOCUMENTS

| | | |
|---|---|---|
| JP | 4033228 B2 | 11/2007 |
| JP | 4069887 B2 | 1/2008 |

(Continued)

*Primary Examiner* — Natalie Huls
*Assistant Examiner* — Monica S Young
(74) *Attorney, Agent, or Firm* — Morgan, Lewis & Bockius LLP

(57) ABSTRACT

An apparatus for controlling an oxygen sensor may include an oxygen sensor configured to measure the exhaust gas which is generated by the combustion of the engine to generate an oxygen signal, and a controller configured to detect, through the oxygen sensor, a lag of the oxygen signal having responsiveness which is reduced depending on an oxygen amount of the exhaust gas, store information on occurrence factors which cause the lag of the oxygen signal, and increase a current heating quantity of a corresponding specific region about the occurrence factors to reconfirm whether the oxygen signal lags and determine the oxygen sensor as a failure or release a failure detection for the oxygen sensor.

14 Claims, 5 Drawing Sheets

(56) References Cited

U.S. PATENT DOCUMENTS

| | | | |
|---|---|---|---|
| 2004/0016228 A1* | 1/2004 | Yasui | G01N 27/4067 60/285 |
| 2004/0069630 A1* | 4/2004 | Tanaka | G01N 27/419 204/424 |
| 2007/0010932 A1* | 1/2007 | Gotoh | F01N 11/00 701/114 |
| 2007/0158333 A1* | 7/2007 | Kosaka | F02D 41/062 219/483 |
| 2009/0319085 A1* | 12/2009 | Sell | F02D 41/1494 700/275 |

FOREIGN PATENT DOCUMENTS

| | | |
|---|---|---|
| JP | 2008-261757 A | 10/2008 |
| KR | 10-2004-0094920 A | 11/2004 |
| KR | 10-0774312 B1 | 11/2007 |
| KR | 10-2008-0032730 A | 4/2008 |
| KR | 10-0896637 B1 | 5/2009 |

\* cited by examiner

APPARATUS AND METHOD FOR CONTROLLING OXYGEN SENSOR

CROSS-REFERENCE(S) TO RELATED APPLICATION(S)

The present application claims priority to Korean Patent Application No. 10-2014-0148131 filed Oct. 29, 2014, the entire contents of which is incorporated herein for all purposes by this reference.

BACKGROUND OF THE INVENTION

Field of the Invention

Various aspects of the present invention relate to an oxygen sensor, and more particularly, to an apparatus and a method for controlling an oxygen sensor capable of performing a diagnosis for detecting a non-behavior of the oxygen sensor.

Description of Related Art

In the typical engine driving apparatus, a fuel pump delivers fuel in a tank up to an injector through a fuel hose when an engine starts and an engine control device drives the injector to inject the fuel. The injected fuel is combusted and then exhaust gas is discharged.

An example of an apparatus which measures an oxygen concentration of the exhaust gas may include an oxygen sensor. The oxygen sensor is installed at a predetermined position of an exhaust manifold. Therefore, the oxygen sensor measures an oxygen ratio in the exhaust gas and notifies an electronic control module (ECM) of the measured oxygen ratio. In this case, the electronic control module (ECM) controls the injector depending on the oxygen ratio to control an air fuel ratio of a mixer which enters the engine.

Further, a resistance value inside the oxygen sensor which reacts to an oxygen amount in the exhaust gas varies depending on a temperature of the sensor. However, since the lower the temperature, the larger the resistance value, a magnitude in an output voltage of the oxygen sensor is reduced. When the magnitude in the output voltage is reduced, the electronic control module (ECM) may not properly distinguish a change in the oxygen amount in the exhaust gas.

Therefore, to keep the temperature of the oxygen sensor constant even in a region in which a temperature of the exhaust gas is low, the ECM controls the heater installed inside the oxygen sensor according to the temperature of the exhaust gas to keep the temperature of the sensor constant.

In this case, when heater performance is reduced and thus the oxygen sensor does not keep a constant temperature, the ECM performs only a fault diagnosis of the oxygen sensor based on a magnitude in internal resistance of the oxygen sensor.

In this case, for the fault diagnosis, it is detected whether the oxygen sensor is out of order based on exhaust gas modeling. The method requires an operation technology which requires much time and/or costs to determine whether the oxygen sensor is out of order.

Further, if it is determined that the oxygen sensor is out of order, the oxygen sensor is replaced by a new product, and therefore there is no room for improving the performance of the oxygen sensor.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing an apparatus and a method for controlling an oxygen sensor capable of improving performance of the oxygen sensor while avoiding an operation technology which requires time and efforts for exhaust gas modeling.

Various aspects of the present invention are additionally directed to an apparatus and a method for controlling an oxygen sensor capable of confirming a specific operation condition region in which heating is not performed well.

Various aspects of the present invention are further directed to providing an apparatus and a method for controlling an oxygen sensor capable of performing heating learning which recovers a signal of the oxygen sensor when the signal of the oxygen sensor lags.

Various aspects of the present invention are directed to providing an apparatus and a method for controlling an oxygen sensor capable of improving performance of the oxygen sensor while avoiding an operation technology which requires time and efforts for exhaust gas modeling.

In accordance with an embodiment of the present invention, an apparatus for controlling an oxygen sensor, may include an oxygen sensor measuring an exhaust gas which is generated by combustion of an engine to generate an oxygen signal, and a controller detecting, through the oxygen sensor, a lag of the oxygen signal having responsiveness which is reduced depending on an oxygen amount of the exhaust gas, storing information on occurrence factors which cause the lag of the oxygen signal, and increasing a current heating quantity of a corresponding specific region about the occurrence factors to reconfirm whether the oxygen signal lags to determine the oxygen sensor as a failure or release a failure detection for the oxygen sensor.

The oxygen sensor may include a heater generating heating quantity depending on a control of the controller, and an element measuring the exhaust gas to generate the oxygen signal.

The controller determines the oxygen sensor as a failure when an increase in the current heating quantity is maximal, and releases the failure detection for the oxygen sensor when the increase in the current heating quantity is not maximal.

The controller again measures the oxygen signal of the oxygen sensor when the oxygen sensor enters a next specific region when the increase in the current heating quantity is determined to be not maximal, to release the failure detection for the oxygen sensor when the responsiveness of the measured oxygen signal is recovered.

The information on the occurrence factors may include at least one of cooling water temperature, revolutions per minute (RPM), intake temperature, load, vehicle speed, and post-starting time.

The oxygen sensor is a $ZrO_2$ oxygen sensor.

The element transmits internal resistance and a lambda voltage which is the oxygen signal, together with the controller.

The information on the occurrence factors is mapped with the heating quantity to confirm a specific operation condition region in which heating may have a preset reference value or less.

In another aspect of the present invention, a method for controlling an oxygen sensor, may include generating exhaust gas by combustion of an engine, measuring, by an oxygen sensor, the exhaust gas to generate an oxygen signal, detecting, by a controller, through the oxygen signal, a lag of the oxygen signal having responsiveness which is reduced depending on an oxygen amount of the exhaust gas, storing, by the controller, information on occurrence factors which cause the lag of the oxygen signal, increasing, by the controller, a current heating quantity of a corresponding specific region for the occurrence factors and reconfirming whether the lag of the oxygen signal occurs, and determining, by the controller, the oxygen sensor as a failure depending on reconfirmation result or releasing, by the controller, a failure detection for the oxygen sensor.

The oxygen sensor may include a heater generating the heating quantity depending on a control of the controller, and an element measuring the exhaust gas to generate the oxygen signal.

The reconfirming may include determining, by the controller, whether an increase in a current heating quantity is maximal, determining, by the controller, the oxygen sensor as a failure when the increase in the current heating quantity is maximal as determination result, and releasing the failure detection for the oxygen sensor when the increase in the current heating quantity is not maximal as the determination result.

The releasing of the failure detection may include measuring again, by the controller, the oxygen signal of the oxygen sensor when the oxygen sensor enters a next specific region when the increase in the current heating quantity is determined to be not maximal, and releasing the failure detection for the oxygen sensor when the responsiveness of the measured oxygen signal is recovered.

The information on the occurrence factors may include at least one of cooling water temperature, revolution per minute (RPM), intake temperature, load, vehicle speed, and post-starting time.

The oxygen sensor is a $ZrO_2$ oxygen sensor.

The element transmits internal resistance and a lambda voltage which is the oxygen signal, together with the controller.

The method may further include mapping occurrence factor information with the heating quantity to confirm a specific operation condition region in which the heating may have a preset reference value or less.

It is understood that the term "vehicle" or "vehicular" or other similar terms as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuel derived from resources other than petroleum). As referred to herein, a hybrid vehicle is a vehicle that has two or more sources of power, for example, both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

Figure 1:
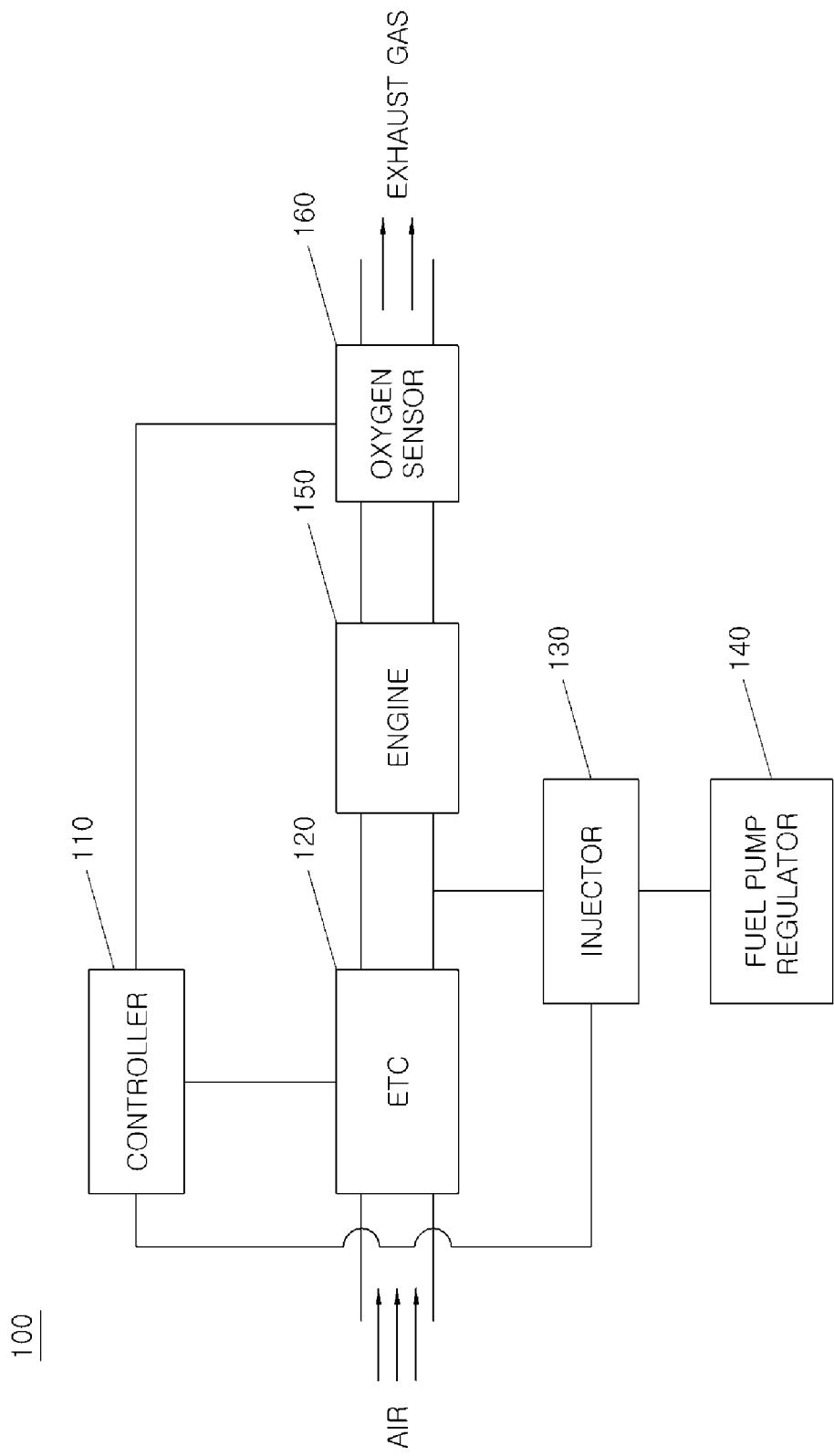
FIG. 1 is a configuration block diagram of an exemplary apparatus for controlling an oxygen sensor according to an exemplary embodiment of the present invention.

FIG. 1 is a configuration block diagram of an apparatus for controlling an oxygen sensor in accordance with various embodiments of the present invention. Referring to FIG. 1, the apparatus for controlling an oxygen sensor is configured to include an engine 150, an oxygen sensor 160 measuring exhaust gas generated by combustion of the engine 150 to generate an oxygen signal, a controller 110 receiving the oxygen signal from the oxygen sensor 160 to determine whether the oxygen sensor is out of order, an electric throttle control (ETC) 120 controlling an air amount depending on a control of the controller 110, an injector 130 controlling an injection quantity of fuel depending on the control of the controller 110, a fuel pump regulator 140 controlling fuel and supplying the controlled fuel to the injector 130, and the like.

The controller 110 uses the oxygen signal to detect a lag of the oxygen signal having responsiveness which is reduced depending on an oxygen amount of the exhaust gas and stores information on occurrence factors which cause the lag of the oxygen signal. Further, the controller 110 increases a current heating quantity of a corresponding specific region about the occurrence factors to reconfirm whether the oxygen signal lags, thereby determining the oxygen sensor as a failure or releasing failure detection for the oxygen sensor.

The electric throttle control (ETC) 120 adjusts an open angle of a throttle valve to control the air amount introduced into the engine 150.

The injector 130 controls a fuel quantity injected into the engine 150. Further, the injector 130 is connected to the fuel pump regulator 140. The fuel pump regulator 140 is connected to a fuel tank, a fuel pump, and the like.

As the engine 150, a gasoline engine may be used but the present invention is not limited thereto, and therefore, the engine 150 is partially changed and thus may be a diesel engine.

The oxygen sensor 160 measures the oxygen amount from the exhaust gas which is generated by combustion of the engine 150 to generate the oxygen signal. The oxygen sensor 160 is called a lambda sensor, in which when a lambda λ is used in a combustion theory, the lambda λ shows an excess air ratio (ratio of air amount required to completely combust fuel to actually supplied air content). In a theoretical air-fuel ratio to completely combust fuel, a value of the lambda λ becomes 1.

In accordance with various embodiments of the present invention, as the oxygen sensor 160, a $ZrO_2$ oxygen sensor is used, but the present invention is not limited thereto.

Therefore, the controller 110 may use the oxygen signal generated by the oxygen sensor 160 to confirm responsiveness of the oxygen sensor 160. In other words, an oxygen amount atmosphere of the exhaust gas is reversed, and as a result, when the oxygen sensor 160 does not react thereto, the lag of the oxygen signal having the reduced responsiveness occurs. It is possible to confirm whether the oxygen sensor 160 is out of order or normal by using the responsiveness.

FIG. 1 schematically illustrates the apparatus for controlling an oxygen sensor to help understand the present invention, but the apparatus for controlling an oxygen sensor includes a cooler, loads (for example, light, and the like), and the like, in addition to the illustrated components.

Figure 2:
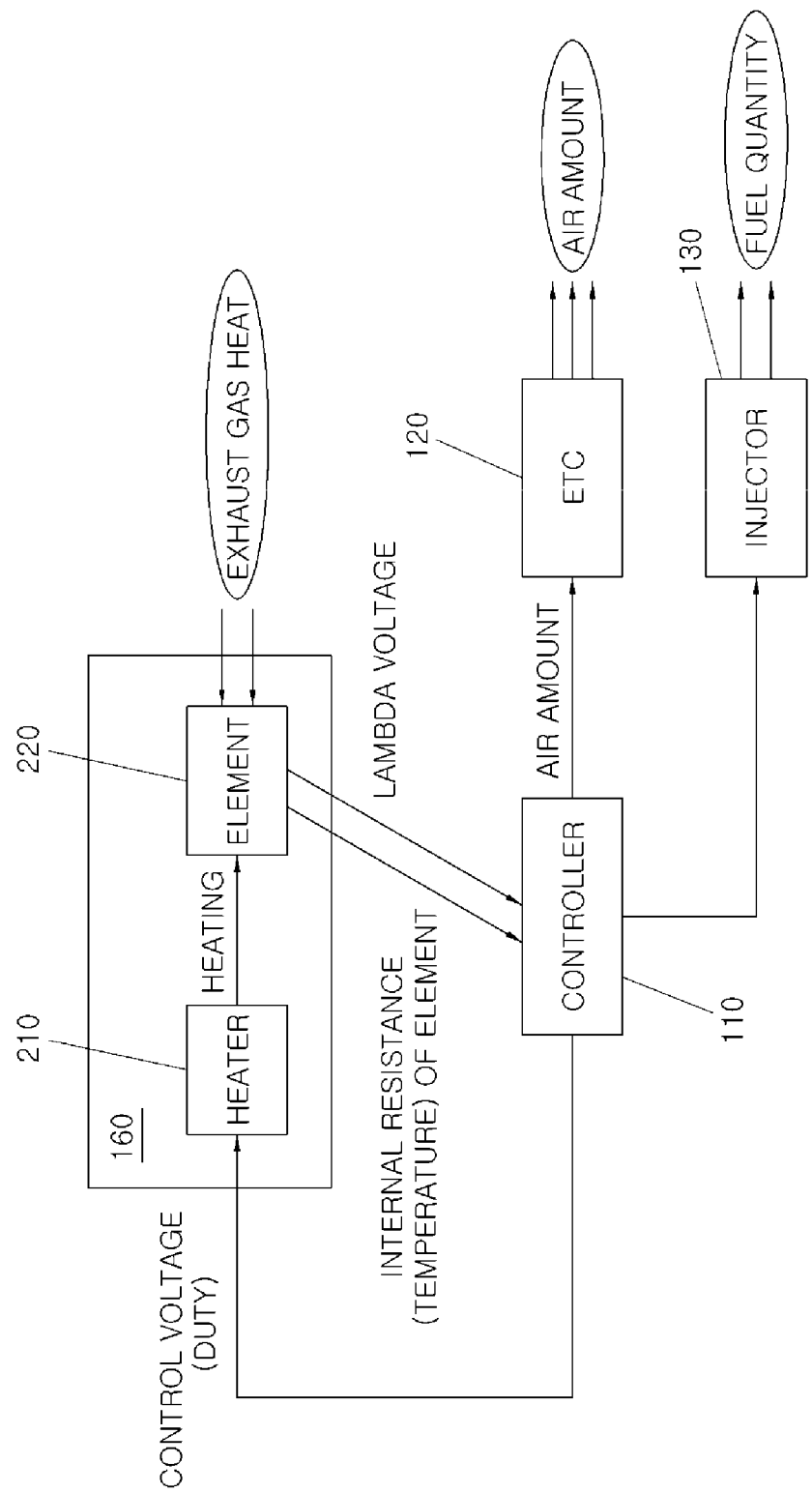
FIG. 2 is a conceptual diagram illustrating an operation of the oxygen sensor illustrated in FIG. 1.

FIG. 2 is a conceptual diagram illustrating an operation of the oxygen sensor 160 illustrated in FIG. 1. Referring to FIG. 2, the oxygen sensor 160 is configured to include a heater 210 and an element 220.

The oxygen sensor 160 reacts to the oxygen amount in the exhaust gas and an internal resistance value of the element 220 varies depending on a sensor temperature. In other words, since the lower the sensor temperature, the larger the resistance value, a magnitude in a lambda voltage (output voltage) of the sensor is reduced. When the magnitude in the lambda voltage is reduced, a change in the oxygen amount in the exhaust gas may be properly distinguished.

Therefore, to keep the temperature of the oxygen sensor 160 constant even in the region in which the temperature of the exhaust gas is low, the heater 210 is installed inside the oxygen sensor. Therefore, the heater 210 is controlled depending on the temperature of the exhaust gas and thus the temperature of the sensor may be kept constant. Further, the heater 210 is controlled depending on the information on the occurrence factors such as cooling water temperature, RPM, intake temperature, load, vehicle speed, and post-starting time, in addition to the temperature of the exhaust gas to control the heating quantity. That is, the controller 110 performs a duty voltage control to control the heating quantity which is generated from the heater 210.

The element 220 transmits the internal resistance (temperature) of the element and/or the lambda voltage to the controller 110.

Figure 3:
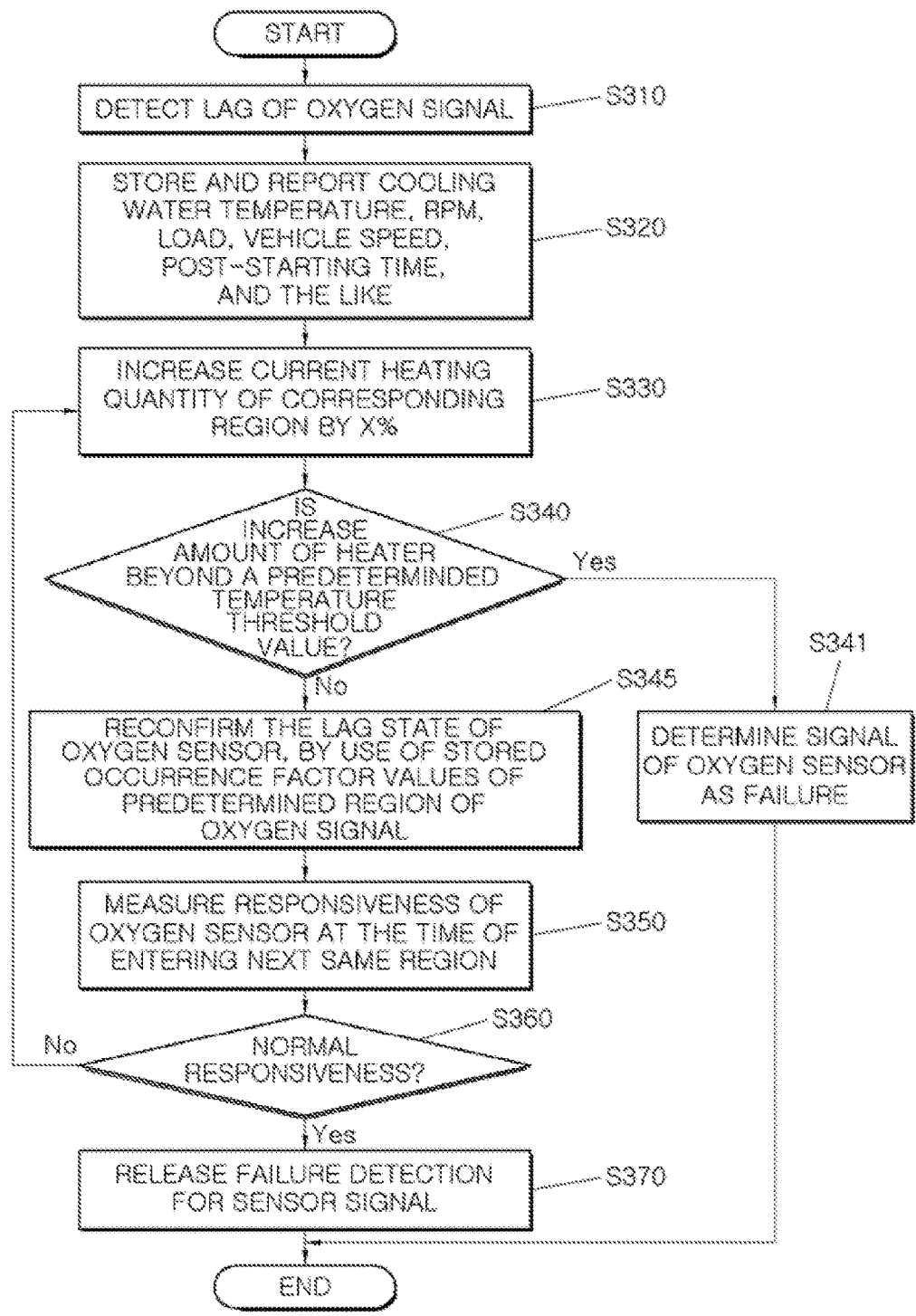
FIG. 3 is a flow chart illustrating an exemplary process of improving performance of the oxygen sensor according to an exemplary embodiment of the present invention.

FIG. 3 is a flow chart illustrating a process of improving the performance of the oxygen sensor in accordance with various embodiments of the present invention. Referring to FIG. 3, when the exhaust gas is generated by the combustion of the engine 150 (FIG. 1), the oxygen sensor 160 (FIG. 1) measures the exhaust gas to generate the oxygen signal.

The controller 110 (FIG. 1) receives the oxygen signal from the oxygen sensor 160 to detect the lag of the oxygen signal having the responsiveness which is reduced depending on the oxygen amount of the exhaust gas (step S310). In other words, there may be the case in which the oxygen amount atmosphere in the exhaust gas is reversed, and as a result, the oxygen sensor 160 has the reduced reaction thereto and therefore the responsiveness is reduced. The occurrence factors which cause the reduced responsiveness may be several. That is, the occurrence factor may include the information on occurrence factors such as cooling water temperature, RPM, vehicle speed, and post-starting time.

Therefore, the controller 110 stores the information on the occurrence factors which cause the lag of the oxygen signal (step S320). In other words, the information on the occurrence factors may include a range of the cooling water temperature, a range of the RPM, and the like. In this case, further, to confirm the specific operation condition region, the information on the occurrence factors is reported to the outside so as to map the information on the occurrence factors with the heating quantity. The reporting may be made through wired or wireless communication.

Next, the controller 110 increases a current heating quantity of the corresponding specific region about the occurrence factor as much as X % (step S330). That is, the heating quantity which is generated by the heater 210 (FIG. 2) is increased by controlling the heater 210 (FIG. 2) of the oxygen sensor 160.

As a result, it is confirmed whether the increase quantity of the heater 210 is maximal (step S340). That is, the aim of the step S340 is to confirm the recovery of the responsiveness of the oxygen sensor 210. In other words, it is confirmed that when the increase quantity of the heater 210 is not maximal, the oxygen sensor 160 recovers the responsiveness and when the oxygen sensor 160 enters the next same region, it is confirmed whether the oxygen sensor 160 shows normal responsiveness by again measuring the responsiveness of the oxygen sensor 160 (steps S345 S350 and S360).

As the confirmation result, in step S360, when the oxygen sensor 160 shows the normal responsiveness, the failure detection for the oxygen sensor 160 is released (step S370).

Unlike this, in step S360, when the oxygen sensor 160 does not show the normal responsiveness, steps S330 to S360 are repeatedly performed.

Meanwhile, in step S340, when the increase quantity of the heater 210 is maximal, the signal of the oxygen sensor 160 is inaccurate, which is determined as a failure (step S341).

Figure 4:
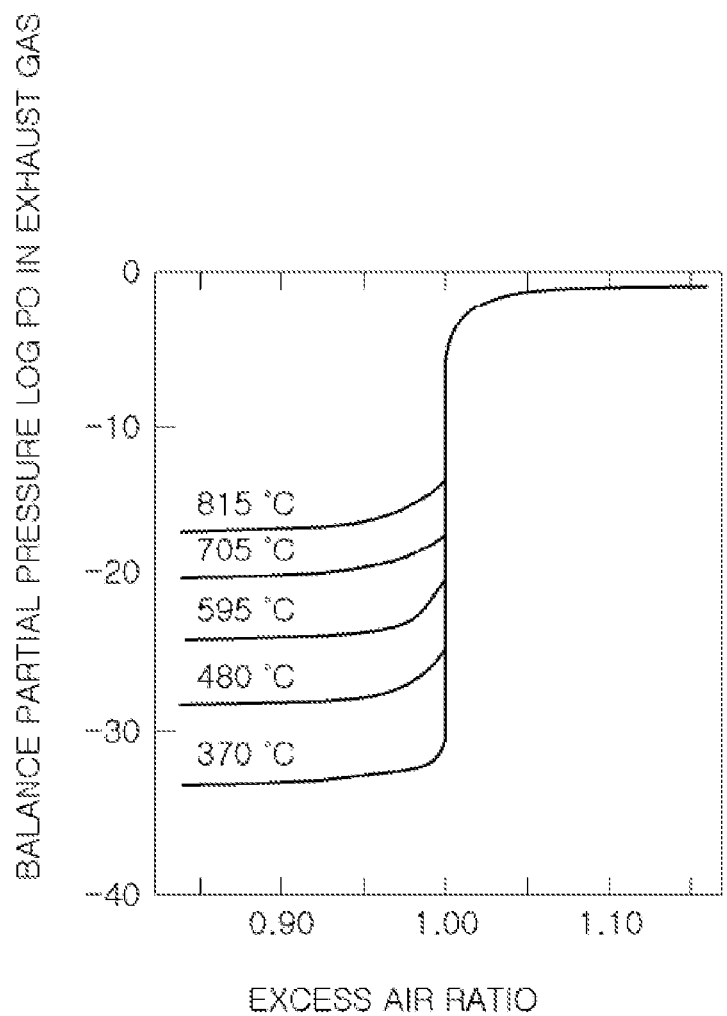
FIG. 4 is a graph generally illustrating a relationship between an excess air ratio as an output characteristic depending on a temperature of the oxygen sensor and a balance oxygen partial pressure according to an exemplary embodiment of the present invention.

FIG. 4 is a graph generally illustrating a relationship between the excess air ratio as an output characteristic depending on the temperature of the oxygen sensor and a balance oxygen partial pressure. Referring to FIG. 4, the performance of the oxygen sensor is determined by characteristics such as a flow rate (diffusion) of the exhaust gas, a catalytic action of an outer electrode, porosity of a platinum electrode, a kind of over coat, and the like. Referring to FIG. 4, in a theory of the excess air ratio, a side at which a mixing ratio is sufficient is left and a side at which a mixing ratio is insufficient is right. Therefore, as the mixing ratio is abundant and the temperature is lack, the balance oxygen partial pressure is low.

Figure 5:
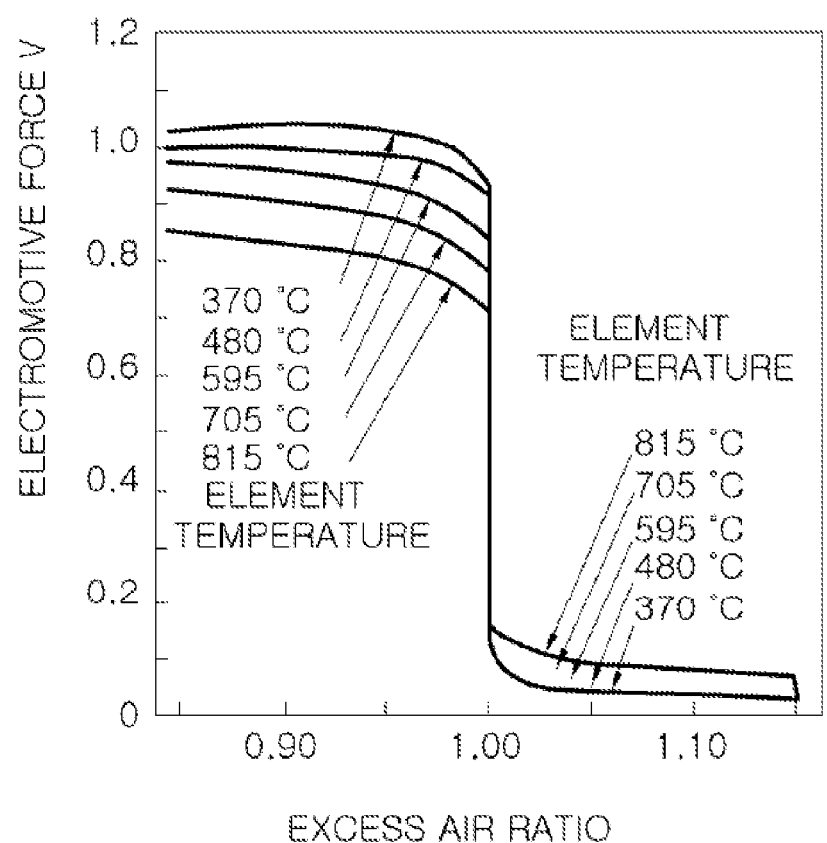
FIG. 5 is a graph generally illustrating a relationship between the excess air ratio as the output characteristic depending on the temperature of the oxygen sensor and an electromotive force according to an exemplary embodiment of the present invention.

FIG. 5 is a graph generally illustrating a relationship between the excess air ratio as the output characteristic depending on the temperature of the oxygen sensor and an electromotive force. Referring to FIG. 5, in a theory of the excess air ratio, a side at which a mixing ratio is abundant is left and a side at which the mixing ratio is lacking is right. Therefore, as the mixing ratio is abundant and the temperature is low, the electromotive force is high.

The electromotive force may be represented by the following Equation.

$$E = RT/4F \ln(P_{O_2}''/P_{O_2}')$$ [Equation 1]

In the above Equation 1,

E: Electromotive force [V]

R: Gas constant 8.31 [J/molK]

T: Absolute temperature [° K] (ceramic temperature)

F: Faraday integer ($9.65 \times 10^4$)

$P_{O_2}''$: Oxygen partial pressure in exhaust gas [Pa] ($\approx 10 \sim 10^{-18}$ KPa)

$P_{O_2}'$: Oxygen partial pressure in the air [Pa]($\approx 21$ KPa)

In accordance with various embodiments of the present invention, it is possible to determine whether the oxygen sensor is out of order while avoiding the operation technology which requires the time and efforts for the exhaust gas modeling.

Further, in accordance with various embodiments of the present invention, it is possible to confirm the specific operation condition region by allowing the controller to perform a report for mapping using the measurable signals such as cooling water temperature, revolution per minute (RPM), intake temperature, load, vehicle speed, and post-starting time.

Further, in accordance with various embodiments of the present invention, it is possible to perform the heating learning which recovers the signal of the oxygen sensor when the signal of the oxygen sensor including the heating learning scheme of products having the reduced heating performance with respect to the production dispersion of the oxygen sensor lags.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. An apparatus for controlling an oxygen sensor, comprising:
   the oxygen sensor configured for measuring an exhaust gas which is generated by combustion of an engine to generate an oxygen signal; and
   a controller configured for detecting, through the oxygen sensor, a lag state of the oxygen signal having responsiveness which is reduced depending on an oxygen amount of the exhaust gas,
      wherein the oxygen signal is monitored, by the controller, for a reversal of the oxygen signal to fuel ratio value and correlated to a change in an occurrence factor including at least one of cooling water temperature, revolution per minute (RPM), intake temperature, load, vehicle speed, and post-starting time,
      wherein the oxygen signal to fuel ratio value is compared, by the controller, to a responsiveness fuel ratio threshold and if exceeded the lag state is declared,
      wherein a value for the changed occurrence factor that initiates the lag state along with a heater temperature value measured from a temperature sensor on an oxygen sensor heater is recorded, by the controller, as a stored value, wherein the stored value is a predetermined region of the oxygen signal;
      wherein the controller is configured to reconfirm if the lag state persists when a condition of the stored value of the predetermined region of the oxygen signal is matched, while the heater temperature value is incrementally increased to a temperature threshold, and
      wherein if the lag state has not shown the reversal of the oxygen signal to fuel ratio exiting the lag state when a heater temperature threshold is met, a failure detection of the oxygen sensor is determined or if the oxygen signal to fuel ratio existing the lag state occurs, a release failure signal is set to allow further monitoring of the oxygen sensor.

2. The apparatus of claim 1, wherein the oxygen sensor includes:
   the oxygen sensor heater configured for generating the heating quantity depending on a control of the controller; and
   an element configured for measuring the exhaust gas to generate the oxygen signal.

3. The apparatus of claim 2, wherein the element transmits internal resistance and a lambda voltage which is the oxygen signal, to the controller.

4. The apparatus of claim 1, wherein the controller is configured to determine the oxygen sensor as a failure when an increase in the heating quantity is beyond a predetermined temperature threshold value, and releases the failure detection for the oxygen sensor when the increase in the heating quantity is below the predetermined temperature threshold value.

5. The apparatus of claim 4, wherein the controller is configured to measure again the oxygen signal of the oxygen sensor when the oxygen sensor enters a next predetermined region when the increase in the heating quantity is determined to be below the predetermined temperature threshold value, and configured to release the failure detection for the oxygen sensor when the responsiveness of the measured oxygen signal is recovered.

6. The apparatus of claim 1, wherein the oxygen sensor is a $ZrO_2$ oxygen sensor.

7. The apparatus of claim 1, wherein the information on the occurrence factor is mapped with the heating quantity to confirm a predetermined operation condition region in which heating has a preset reference value or less.

8. A method for controlling an oxygen sensor, comprising:
   generating exhaust gas by combustion of an engine;
   measuring, by the oxygen sensor, the exhaust gas to generate an oxygen signal;
   detecting, by a controller, through the oxygen signal, a lag state of the oxygen signal having responsiveness which is reduced depending on an oxygen amount of the exhaust gas;
   monitoring the oxygen signal, by the controller, for a reversal of the oxygen signal to fuel ratio value and correlating the oxygen signal to a change in an occurrence factor including at least one of cooling water temperature, revolution per minute (RPM), intake temperature, load, vehicle speed, and post-starting time,
   comparing the oxygen signal to fuel ratio value, by the controller, to a responsiveness fuel ratio threshold and if exceeded the lag state is declared, recording a value for the changed occurrence factor that initiates the lag state along with a heater temperature value measured from a temperature sensor on an oxygen sensor heater, by the controller, as a stored value, wherein the stored value is a predetermined region of the oxygen signal;

reconfirming, by the controller, if the lag state persists when a condition of the stored value of the predetermined region of the oxygen signal is matched, while the heater temperature value is incrementally increased to a temperature threshold, and determining, by the controller, a failure detection of the oxygen sensor if the lag state has not shown the reversal of the oxygen signal to fuel ratio exiting the lag state when a heater temperature threshold is met, or setting a release failure signal to allow further monitoring of the oxygen sensor if the oxygen signal to fuel ratio existing the lag state occurs.

9. The method of claim 8, wherein the oxygen sensor includes:
the oxygen sensor heater generating the heating quantity depending on a control of the controller; and
an element measuring the exhaust gas to generate the oxygen signal.

10. The method of claim 9, wherein the element transmits internal resistance and a lambda voltage which is the oxygen signal, to the controller.

11. The method of claim 8, wherein the reconfirming includes:

determining, by the controller, whether an increase in the heating quantity is beyond a predetermined temperature threshold value;

determining, by the controller, the oxygen sensor as a failure when the increase in the heating quantity is beyond the predetermined temperature threshold value as determination result; and releasing the failure detection for the oxygen sensor when the increase in the heating quantity is below the predetermined temperature threshold value as the determination result.

12. The method of claim 11, wherein the releasing of the failure detection includes:
measuring again, by the controller, the oxygen signal of the oxygen sensor when the oxygen sensor enters a next predetermined region of the oxygen signal when the increase in the heating quantity is determined to be below the predetermined temperature threshold value; and
releasing the failure detection for the oxygen sensor when the responsiveness of the measured oxygen signal is recovered.

13. The method of claim 8, wherein the oxygen sensor is a $ZrO_2$ oxygen sensor.

14. The method of claim 8, further comprising:
mapping occurrence factor information with the heating quantity to confirm a predetermined operation condition region in which the heating has a preset reference value or less.

* * * * *